United States Patent [19]
Sugiyama et al.

[11] Patent Number: 5,948,895
[45] Date of Patent: Sep. 7, 1999

[54] PROCESS FOR PRODUCING A GLYCOSYLATED AMINO COMPOUND

[75] Inventors: Koji Sugiyama; Akane Ohnaka, both of Kyoto, Japan

[73] Assignee: Kyoto Daiichi Kagaku Co., Ltd., Kyoto, Japan

[21] Appl. No.: 08/893,161

[22] Filed: Jul. 15, 1997

[30]     Foreign Application Priority Data

Jul. 15, 1996 [JP] Japan .................................. 8-184976

[51] Int. Cl.$^6$ ............................................. A61K 38/14
[52] U.S. Cl. .................... 530/395; 530/322; 530/345; 530/402; 514/8
[58] Field of Search ................... 530/322, 333, 530/345, 395, 402; 514/2, 8

[56]           References Cited

U.S. PATENT DOCUMENTS

| | | | |
|---|---|---|---|
| 3,919,317 | 11/1975 | Huff .................................. | 260/566 R |
| 4,508,921 | 4/1985 | Amato .................................. | 562/443 |
| 5,032,405 | 7/1991 | Huang .................................. | 424/463 |
| 5,122,367 | 6/1992 | Ron .......................................... | 424/80 |
| 5,583,140 | 12/1996 | Beucherif .............................. | 514/299 |
| 5,614,487 | 3/1997 | Battersby ................................ | 514/2 |
| 5,656,721 | 8/1997 | Albert .................................... | 530/300 |

OTHER PUBLICATIONS

Abstract of: Mora, M.S. et al., Developments in Biological Standardization vol. 74, 295–303, 1992.

E. Schleicher et al., "Specific Quantitation by HPLC of Protein (Lysine) Bound Glucose in Human Serum Albumin and Other Glycosylated Proteins", *J. Clin. Chem. Clin. Biochem.*, vol. 19, pp. 81–87.

K. A. Mereish et al., "Glucosylated Albumin and its Influence on Salicylate Binding", *Journal of Pharmaceutical Sciences*, vol. 71, No. 2, pp. 235–238.

Marc Rendell et al., "Aminophenylboronic Acid Affinity Chromatography and Thiobarbituric Acid Colorimetry Compared for Measuring Glycated Albumin", *Clincal Chemistry*, vol. 31, No. 2, pp. 229–234.

Marc Rendell et al., "Use of aminophenylboronic acid affinity chromatography to measure glycosylated albumin levels", *J Lab Clin Med*, vol. 105, No. 1, pp. 63–69.

Yasuo Ohe et al., "Radioimmunoassay of glycosylated albumin with monoclonal antibody to glucitol–lysine", *Clinica Chimica Acta*, pp. 229–238.

Jencks, Catalysis in Chem & Enz, pp. 182–193, 1969.

Kunz, Angew Chem Int Ed. 26, 294, 1987.

*Primary Examiner*—Cecilia J. Tsang
*Assistant Examiner*—David Lukton
*Attorney, Agent, or Firm*—Merchant & Gould P.C.

[57]           ABSTRACT

A process which makes possible to produce a glycosylated amino compound (e.g. protein) easily in short period without denaturation of protein. The sugar (e.g. glucose) and protein (e.g. serum) are mixed, and the mixture is dried under reduced pressure, so that sugar and protein quickly react with each other to produce the glycosylated protein. The drying under reduced pressure is preferably lyophilization which is conducted under the following conditions: the temperature is about −20° C., the pressure is about 2 mmHg, and the treatment time is 12 hours. Unreacted glucose is then removed by the dialysis process, thus providing the required glycosylated protein sterilization need not be carried out. This process makes it possible to produce a glycosylated protein in about one day as compared to 7 days by the conventional process, so that the denaturation of protein is less likely to occur.

12 Claims, No Drawings

PROCESS FOR PRODUCING A GLYCOSYLATED AMINO COMPOUND

FIELD OF THE INVENTION

The present invention relates to a process for producing a glycosylated amino compound such as glycosylated protein.

BACKGROUND OF THE INVENTION

Glycosylated amino compounds consist of sugar and amino compounds bonded by non-enzymatic covalent bonds, so that glycosylated amino compounds are also called "saccharic amino compounds." Glycosylated proteins are one group of such compounds, and are produced in the food industry or for medical applications. Recently, glycosylated proteins have been used as markers for clinical examinations, since, in the human body, the concentration of glycosylated protein depends on the concentration of sugar which existed together with protein for a certain period in the past. The period depends on the average life time of the protein.

For example, the concentration of glycosylated hemoglobin, which is produced by the reaction between blood glucose and blood hemoglobin, depends on the average concentration of blood glucose one or two months previously. Moreover, the concentration of glycosylated albumin, which is produced by the reaction between blood glucose and serum albumin, depends on the average concentration of blood glucose one or two weeks previously. Therefore, in order to determine the past value of blood sugar of diabetic patients, the concentrations of glycosylated hemoglobin and glycosylated albumin in the blood of the patients are measured.

In order to measure a glycosylated protein in the human body with a high accuracy, a glycosylated protein is needed as a standard sample for controlling the measurement accuracy. Therefore, in the blood sugar examination for diabetics, glycosylated hemoglobin and glycosylated albumin of optionally determined concentration are produced artificially and used as a standard sample.

As the general process for producing the glycosylated protein for controlling the measurement accuracy, sugar and protein are mixed and the mixture is reacted by incubation at approximately 37° C. for about seven days (See processes described in, for example, Mark Rendell et al, J.Lab. Cli. Med. 105, 63–69 (1985); and E. Schleicher and O. H. Wieland, J. Cli. Chem. Cli. Biochem. 19, 81–87 (1981) etc).

However, the conventional process for producing a glycosylated protein needs a long incubation step of about seven days. In addition, if it takes a long time to produce the glycosylated protein, samples containing the protein might be putrefied. In order to prevent this, the conventional process generally includes a sterilization step, but this complicates the process. In addition, a long incubation period is liable to cause the denaturation of protein.

SUMMARY OF THE INVENTION

To solve the above-mentioned problems, the invention provides a process which makes it possible to produce a glycosylated amino compound easily in a short period without denaturation of amino compounds (e.g. proteins).

The process for producing a glycosylated amino compound of the present invention comprises mixing a sugar with an amino compound in the presence of a solvent and drying the mixture under reduced pressure.

Thus, the process of this invention is completed within approximately one day, under gentle conditions, so that the putrefaction and denaturation of protein or the like are prevented.

In the present invention, the mixture is usually solution, however it may be sol or the like. The solvent is usually water or a buffer solution. The buffer solution has a pH in a range to prevent amino compounds from denaturation. To be concrete, the buffer solution is usually in the pH 5 to 9 region. Examples of the type of the buffer solution are triethanolamine hydrochloride buffer, Tris-HCl buffer, phosphate buffer, Good's buffer, and the like. The buffer solution is prepared by a conventional method.

In the present invention, an amino compound broadly denotes a compound containing an amino group. Examples of amino compounds include proteins, peptides and amino acids.

In the present invention, "sugar" includes not only "simple sugars" such as monosaccharides and condensation products of monosaccharides, namely, oligosaccharides and polysaccharides, but also "complex sugars" obtained by linking sugar with other materials.

Moreover, in the present invention, "protein" denotes polymers containing nitrogen in which amino acids are linked via a peptide linkage. In addition, as mentioned below, since the linkage between sugar and protein is thought to be a dehydration condensation reaction of an amino group with carbonyl group or ketone group, not only proteins but also amino compounds containing amino groups, for example, amino acids and peptides or the like, can be produced by the process of the present invention.

In the present invention, "reduced pressure" denotes a pressure below atmospheric pressure. The pressure, for example, is in the range of 0.05 to 5 mmHg. This treatment time is, for example, in the range of 6 to 8 hours.

It is preferable that the above mentioned drying under reduced pressure is a lyophilization, since the drying time is shortened. In the lyophilization, the freezing temperature is, for example, in the range of −10 to −50° C., and the other conditions such as pressure etc. are the same as the above.

It is preferable that unreacted sugar is removed after drying under reduced pressure. This is because the concentration of glycosylated protein may vary with the reaction of the unreacted sugar with unreacted protein, so that the glycosylated protein content is not reliable when it is used as a standard sample in the measurement.

Further in the process of the present invention, it is preferable that the sugar is at least one of the group consisting of monosaccharides, oligosaccharides, and polysaccharides; and the protein is at least one of the group consisting of hemoglobin, albumin, globulin, fibrinogen, fibrin and lipoprotein.

Moreover, in the process of the present invention, it is preferable that sugar phosphate is used as sugar.

DETAILED DESCRIPTION OF THE INVENTION

The present invention will be described in detail as follows.

First, the general reaction mechanism of sugar with protein will be explained.

When sugar is mixed with protein, dehydro-condensation occurs between an amino group of the protein and an aldehyde group or ketone group of the sugar. Moreover, a hydroxyl group near the aldehyde or ketone group isomerizes, thereby generating a glycosylated protein that is transformed into stable ketose type amine. All these reactions proceed by a nonenzymatic process. We presume that such reaction is generated in the glycosylated protein producing process of the present invention because the reaction is general. Moreover, we assume that the reaction mechanism is applicable to the reaction between sugar and other amino compounds, such as amino acids, peptides or the like.

Next, the process for producing the glycosylated amino compound of the present invention will be described. The following is an example of the process for producing glycosylated protein.

Sugar is first mixed with protein. Usually the protein is provided as a protein solution.

The preferred examples of the sugar and protein are described above. However, in the case of producing the glycosylated protein for the accuracy control of a blood sugar determination, in general, glucose is used as the sugar and serum protein is used as the protein. The serum protein preparation or serum itself may be used for the protein.

The concentration of the protein is not critical. However, in the case of producing glycosylated protein for controlling the accuracy of determination of blood sugar, it is preferable that the concentration of the protein is the same as that in the blood of a living body. For example, the concentration of blood hemoglobin is in the range of 120 to 160 mg/ml; the concentration of serum albumin is in the range of 35 to 45 mg/ml.

The weight ratio of the glucose mixed with the protein is not particularly limited. The concentration of produced glycosylated protein depends on the concentration of added glucose, so that the weight ratio of glucose is the same as or above the weight ratio of glycosylated protein intended to be produced.

The mixture of protein and sugar (in general, the mixture is solution) is then dried under reduced pressure, and more preferably is lyophilized. The drying conditions, such as temperature, pressure and hours etc., are not critical, so that the conventionally known conditions can be used. The general pressure condition is as described above. We presume that the mixture solution is condensed and the concentrations of sugar and protein rise in the step of drying under reduced pressure, thus increasing the reaction rate between them, so that the above mentioned condensation reaction occurs quickly. In general, the drying under reduced pressure is completed in 6 to 18 hours.

In addition, unreacted glucose may be removed if necessary. Unreacted glucose is removed by using the molecular size difference between the sugar and the protein. The preferred methods of removing unreacted glucose include dialysis, ultrafiltration, gel permeation chromatography (GPC) or the like. However, the process is not limited to them alone.

If the glycosylated protein is required in powder form, the lyophilization may be conducted again after removing unreacted glucose.

Moreover, if we use an amino acid or peptide instead of the protein in the above-noted process, we can obtain glycosylated amino acid or glycosylated peptide.

The glycosylated protein obtained by the above-noted process has high quality without putrefaction and denaturation, since the process is carried out in a short period under mild conditions.

The invention will be further described below Example and Comparative Example, but it is not limited to them alone.

EXAMPLE

Glucose (special grade, produced by Nacalai tesque) was mixed with serum in glucose contents of 100 to 1000 mg/ml as shown in the following Table 1. The serum was collected from healthy humans. 1 ml of each mixture was placed in a respective vial, and was lyophilized under the following conditions: the cooling temperature was −20° C., the pressure was 2 mmHg, and the treatment time was 12 hours. The lyophilized mixture was dissolved in 1 ml of distilled water, and then 0.5 ml of each solution was respectively placed into a commercial dialysis tube. This dialysis tube was immersed into 3 liters of physiological saline solution (0.9% NaCl aqueous solution), and stirred for 12 hours. Thus unreacted glucose was removed by the dialysis process. Then, the concentration of glucose in serum was measured by the use of Glucose AUTO&STAT GA-1120 (produced by Kyoto Daiichi Kagaku Co., Ltd.), and the value was 0 mg/1ml in all samples.

The amount of glycosylated albumin in the serum after dialysis was measured by the use of Hi-AUTO GAA-2000 (produced by Kyoto Daiichi Kagaku Co., Ltd.). The same experiment without lyophilization was conducted as a comparative example, and the amount of glycosylated albumin was measured. The results are shown in Table 1.

TABLE 1

| Concentration of Glucose (mg/ml) | Comparative Example without lyophilization | | Example with lyophilization | |
|---|---|---|---|---|
| | Value of GA (%) | Glu. (mg/ml) | Value of GA (%) | Glu. (mg/ml) |
| 0 | 19.0 | 59 | 21.5 | 54 |
| 100 | 19.0 | 165 | 25.0 | 150 |
| 200 | 19.3 | 262 | 27.0 | 237 |
| 300 | 19.4 | 350 | 27.5 | 325 |
| 500 | 19.2 | 555 | 29.8 | 520 |
| 1000 | 19.7 | 1052 | 31.6 | 1018 |

Value of GA (%): the concentration of glycosylated albumin in the serum after dialysis
Glu. (mg/ml): the concentration of blood glucose before lyophilization As shown in Table 1, glucose and albumin were reacted in a short lyophilization for 12 hours and glycosylated albumin was produced. Moreover, as the concentration of added glucose increases, the concentration of glycosylated albumin produced after lyophilization increases. On the other hand, in the comparative example in which the lyophilization was not conducted, even if the concentration of added glucose increases, the amount of glycosylated albumin in serum was hardly changed. According to the results, glycosylated albumin was not readily produced by the reaction between glucose and albumin for such a short time as 12 hours if the lyophilization was not used.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method for increasing the rate of formation of a glycosylated amine, wherein the glycosylated amine is obtained by reacting a sugar with an amine in aqueous solution, and wherein the amine is selected from the group consisting of an amino acid, a peptide and a protein;

said method comprising the step of initiating water removal under reduced pressure prior to completion of the glycosylation.

2. The method according to claim 1, wherein the sugar is selected from the group consisting of a monosaccharide, an oligosaccharide, and a polysaccharide.

3. The method according to claim 1, wherein the sugar is a sugar phosphate.

4. The method according to claim 1, wherein the sugar is glucose.

5. The method according to claim 1, wherein the water is removed by lyophilization.

6. The method according to claim 5, further comprising removing unreacted sugar subsequent to the lyophilization.

7. A process for producing a glycosylated protein comprising reacting a sugar and a protein in a solvent while concommitantly removing the solvent under reduced pressure, whereby the rate of glycosylation is increased as a result of the solvent removal, and wherein said protein is selected from the group consisting of hemoglobin, albumin, globulin, fibrinogen, fibrin and a lipoprotein.

8. The method according to claim 7, wherein the sugar is selected from the group consisting of a monosaccharide, an oligosaccharide, and a polysaccharide.

9. The method according to claim 7, wherein the sugar is a sugar phosphate.

10. The method according to claim 7, wherein the sugar is glucose.

11. The process according to claim 7, wherein the solvent is water and its removal is achieved by lyophilization.

12. The process according to claim 7, further comprising removing unreacted sugar subsequent to the solvent removal.

* * * * *